United States Patent [19]

Ihrman

[11] Patent Number: 5,057,625
[45] Date of Patent: Oct. 15, 1991

[54] SELECTIVE ALKYLATION PROCESS

[75] Inventor: Kryn G. Ihrman, Baton Rouge, La.

[73] Assignee: Ethyl Corporation, Richmond, Va.

[21] Appl. No.: 481,173

[22] Filed: Feb. 20, 1990

[51] Int. Cl.$^5$ ............................................... C07C 45/00
[52] U.S. Cl. ..................................... 564/409; 502/152
[58] Field of Search ........................................ 564/409

[56] References Cited

U.S. PATENT DOCUMENTS

| | | | |
|---|---|---|---|
| 3,123,644 | 3/1964 | Olin | 564/409 |
| 3,759,997 | 9/1973 | Napolitano | 564/409 |
| 3,923,892 | 12/1975 | Klopfer | 564/409 |

FOREIGN PATENT DOCUMENTS

| | | | |
|---|---|---|---|
| 1117764 | 1/1959 | France | 564/409 |

*Primary Examiner*—Glennon H. Hollrah
*Assistant Examiner*—Scott C. Rand
*Attorney, Agent, or Firm*—Richard J. Hammond; Joseph D. Odenweller; Edgar E. Spielman, Jr.

[57] ABSTRACT

Mono-ar-tert-butyl toluenediamine is selectively made by heating a mixture of toluenediamine and an aluminum halide of the formula $R_nAlX_{3-n}$ or $R_3Al_2X_3$ wherein n is 0, 1 or 2 and R is an alkyl containing 1-10 carbon atoms to 150°-225° C. and reacting the mixture with isobutylene at 500-300 psig until the yield of mono-ar-tert-butyl toluene is at or near maximum. Minor amounts of di-tert-butyl toluenediamines which form and are difficult to separate can then be lowered by venting the reaction and continuing to heat at about 130°-200° C. until the di-tert-butyl components are decreased to the desired level forming additional mono-ar-tert-butyl toluenediamine.

16 Claims, No Drawings

SELECTIVE ALKYLATION PROCESS

BACKGROUND

Mono-ar-tert-butyl toluenediamine is a known compound useful as a polyurethane chain extender. Burgoyne, et al. U.S. Pat. No. 4,745,223 and U.S. Pat. No. 4,816,543 describe a process for mono-tertbutylating toluenediamine (hereinafter "TDA") using an acidic zeolite catalyst over a very long reaction time.

Stroh, et al. *Angew. Chemie*, 69, Nr 4, (1957) pp. 124–131, describe the ethylation of TDA using aluminum anilide as the catalyst to form almost exclusively ar, ar-diethyl isomers of toluenediamines. (Note: "ar" is a conventional designation for aromatic ring substitution) When aluminum chloride is included with the aluminum anilide as a co-catalyst, the ethylation goes quantitatively to ar, ar-diethyl toluenediamines.

Stroh, et al. also report the butylation of aniline and toluidine with aluminum anilides and with aluminum chloride, montmorillonite or boron trifluoride catalysts but do not describe butylation of aromatic diamines. Similar results are reported in Stroh, et al. U.S. Pat. No. 3,275,690.

SUMMARY

It has now been discovered that mono-ar-tert-butyl toluenediamines can be selectively prepared by heating a mixture of toluenediamine and an aluminum halide which term includes alkylaluminum halides, mixtures of trialkylaluminum and mixtures of aluminum alkyls plus hydrogen halides.

DESCRIPTION OF THE PREFERRED EMBODIMENTS

A preferred embodiment of the invention is a process for making mono-tert butyltoluenediamine, said process comprising: (A) forming a mixture of toluenediamine and an aluminum halide having the formula $R_nAlX_{3-n}$ or $R_3Al_2X_3$ or mixtures thereof, wherein R is an alkyl group containing 1–10 carbon atoms, X is chlorine or bromine and n is 0, 1 or 2 wherein the ratio of moles of toluenediamine:equivalents of Al:equivalents of X is in the range of 5–20:1.0:1–3, reacting said mixture with isobutylene at a temperature of about 150°–220° C. and a pressure of about 500–3000 psig until the mono-tert-butyl toluenediamine content of the reaction mixture is substantially maximized, and recovering said mono-tert-butyl toluenediamine.

In the above ratio, an equivalent of Al means an atom equivalent of Al. An equivalent of halide means an atom equivalent of halide. For example, one mole of diethylaluminum chloride is one equivalent of aluminum and one equivalent of chloride. One mole of ethylaluminum sesquichloride is 2 equivalents of aluminum and 3 equivalents of chlorine. One mole of aluminum chloride is one equivalent of aluminum and 3 equivalents of chlorine.

Suitable aluminum halides include aluminum trihalide, alkylaluminum dihalides, dialkylaluminum halides and alkylaluminum sesquihalides. Examples of these are aluminum trichloride, aluminum tribromide, aluminum trifluoride, dimethylaluminum chloride, dimethylaluminum bromide, diethylaluminum chloride, diethylaluminum bromide, di-n-butylaluminum chloride, di-octylaluminum bromide, di-decylaluminum chloride, methylaluminum dibromide, ethylaluminum dichloride, n-propylaluminum dichloride, n-butylaluminum dichloride, octylaluminum dibromide, decylaluminum dichloride, methylaluminum sesquichloride, ethylaluminum sesquichloride, n-butylaluminum sesquibromide and the like, including mixtures thereof.

Instead of adding the above alkylaluminum halides, it is equivalent to add a trialkylaluminum or low-halide alkylaluminum halide and also add an aluminum trihalide or hydrogen halide to increase the halogen:aluminum ratio. Also, the trialkylaluminum or low-halide alkylaluminum halide can be pre-mixed with an aluminum halide or hydrogen halide which will react to form a mixture of higher-halide alkylaluminum halide. In another equivalent embodiment, TDA can be treated with aluminum metal to form an aluminum anilide-type derivative of TDA and then aluminum halide or hydrogen halide added to obtain the required aluminum/halide ratio in the alkylation mixture. The more preferred aluminum:halide atom ratio is in the range of 1:2–3.

The amount of aluminum halide catalyst should be a catalytic amount. The amount is expressed in terms of moles of TDA per atom of aluminum. A useful ratio is about 5–30/1. A preferred ratio is about 5–20/1.

The process is conducted by heating the toluenediamine (TDA) mixture containing the aluminum halide to about 150°–220° C. If the aluminum halide added is an alkylaluminum halide, an alkane will be evolved during heat-up as the alkylaluminum halide reacts with the TDA. The reacting vessel is pressurized with isobutylene to about 300–5000 psig, more preferably, 500–3000 psig and most preferably about 1000 psig. The amount of isobutylene required to do this will vary with reactor free-space so it is not an independent variable. The ideal reaction stoichiometry is about 1 mole isobutylene per mole of TDA but of course much more isobutylene will be required to bring the reaction vessel to proper pressure.

The preferred reaction temperature is about 150°–220° C. A more preferred reaction temperature is about 160°–210° C. and most preferably about 170°–200° C.

The reaction is continued until the concentration of mono-ar-tert-butyl toluenediamine in the reaction mixture stabilizes. This usually takes about 3–8 hours. Excellent results are usually achieved in about 4 hours.

The final reaction mixture contains about 40–60 percent mono-ar-tert-butyl toluenediamine, about 20–30 percent unreacted TDA, 3–8 percent N,ar-di-tert-butyl toluenediamine and 3–5 percent di-ar-tert-butyl toluenediamine. In a highly preferred embodiment the reaction vessel is vented at the conclusion of the butylation reaction and held at an elevated temperature during a dealkylation period. This elevated temperature is about 130°–200° C. A preferred dealkylation temperature is about 140°–190° C. and most preferably about 150°–175° C. The most labile tert-butyl group appears to be the N-tert-butyl group and this group is selectively dealkylated forming additional mono-ar-tert-butyl toluenediamine. At the same time, some of the di-ar-tert-butyl toluenediamine also dealkylates forming some mono-ar-tert-butyl-toluenediamine. The vented dealkylation period should be continued as long as the concentration of mono-ar-tert-butyl toluenediamine is increasing. This can be about 30 minutes up to about 4 hours. Monitoring of the reaction composition with a gas chromatograph readily detects the optimum time to terminate the dealkylation phase of the process.

Following the dealkylation stage the product is recovered by conventional means. This can be done by washing the reaction mixture with strongly basic water to remove the aluminum and then distilling to recover mono-ar-tert-butyl-toluenediamine. The TDA which distills off first can be recycled.

The following Examples serve to show the manner in which the process can be conducted.

Example 1

Comparative Example

In this Example the aluminum catalyst was formed by adding triethylaluminum to the TDA resulting in a halogen-free catalyst.

In a flask was placed 122 g (1 mole) of TDA. While stirring under a nitrogen atmosphere, 20.8 g (0.182 mole) of trialkylaluminum was added dropwise. Evolved ethane was vented. The mixture was heated and held at 150° C. for 15 minutes. It was then cooled to room temperature and charged under nitrogen into a stainless steel autoclave. It was heated to 199° C. over a 70 minute period while pressurizing with isobutylene to 975 psig. After 3 hours and 50 minutes at 196°–201° C., little pressure drop was observed. Reaction temperature was increased to 220° C. at 1040 psig. After 3 hours the heat was turned off and a sample of product was analyzed by gas chromatography to contain only 4.39 percent mono-ar-tert-butyl toluenediamine.

Example 2

The Invention

Toluenediamine (125.3 g) was placed in a glass flask and maintained under a nitrogen atmosphere. While stirring, 22.5 g of diethylaluminum chloride was added dropwise. Evolved ethane was vented. The solution was then placed in a stainless steel autoclave and heated to 194° C. over a 1 hour 45 minute period while pressurizing to about 1000 psig with isobutylene. Stirring at 1000 psig and about 200° C. was continued for 6 hours at which time the reaction mixture analyzed 41.39 percent mono-ar-tert-butyl toluenediamine. The heat and stirring were turned off overnight. The following day the reaction mixture was heated to about 200° C. at 1000 psig isobutylene and the reaction was continued for 2 hours and 45 minutes. At that time the reaction mixture was 49.26 percent mono-ar-tert-butyl toluenediamine. The reaction was discontinued. Product can be recovered by basic water wash and distillation.

Example 3

This run was made in the same manner as Example 2 except ethylaluminum dichloride was used as the aluminum halide and the TDA/aluminum/chloride ratio was 5.5 moles/1 equiv./2 equiv. The butylation was conducted at 185° C. and 1000 psig isobutylene for 6 hours. The product analyzed:

| TDA | 22.31% |
| N-tert-butyl TDA | 10.55% |
| ar-tert-butyl TDA | 55.19% |
| N,ar-di-tert-butyl TDA | 7.53% |
| ar,ar-di-tert-butyl TDA | 4.41% |

Example 4

This run was the same as in Example 3 except that the butylation reaction was 5 hours at 185° C., 1000 psig. The temperature was then lowered to 150° C. and the autoclave was vented. Stirring was continued at 150.C for 4 hours under vent conditions. Analysis at end of alkylation and end of dealkylation were as follows:

|  | End of Alkylation | End of Dealkylation |
|---|---|---|
| TDA | 21.22 | 29.63 |
| N-tert-butyl TDA | 10.48 | 6.81 |
| ar-tert-butyl TDA | 55.26 | 58.08 |
| N,ar-di-tert-butyl TDA | 7.98 | 2.23 |
| ar,ar-di-tert-butyl TDA | 4.59 | 2.97 |

The results show a substantial increase in ar-tert-butyl toluenediamine during the dealkylation reaction. They also show a sharp drop in the amount of N,ar-di-tert-butyl toluenediamine and ar,ar-di-tert-butyl toluenediamine. The amount of TDA increased substantially which gives a significant economic advantage to the process since TDA can be recycled.

Example 5

This run was similar to Example 4 except ethylaluminum sesquichloride was the aluminum source and the ratio was 7.5 moles TDA/1 equiv. Al/1.5 equiv. Cl. Alkylation with isobutylene was conducted at 201°–220° C. and 1000 psig for 8 hours. The reaction was then cooled to 172° C. and vented. Stirring was continued at 172° C. under vent conditions for 3 hours. The following table shows the key analysis results.

|  | End of Alkylation | End of Dealkylation |
|---|---|---|
| TDA | 30.01 | 34.07 |
| N-tert-butyl TDA | 10.12 | 6.61 |
| ar-tert-butyl TDA | 51.38 | 54.33 |
| N,ar-di-tert-butyl TDA | 4.81 | 2.06 |
| ar,ar-di-tert-butyl TDA | 2.96 | 2.46 |

Again there was a significant increase in the content of mono-ar-tert-butyl toluenediamine during the dealkylation period. There was also a drop in N,ar-di-tert-butyl TDA and ar,ar-di-tert-butyl TDA and a concurrent increase in TDA.

Example 6

In this Example the aluminum source was aluminum chloride and the resultant ratio was 10 moles TDA/1 equiv. Al/-3 equiv. Cl. The alkylation was conducted at 170° C. for only 3 hours. Reaction mixture was analyzed hourly as follows:

|  | Alkylation Time | | |
|---|---|---|---|
|  | 1 Hour | 2 Hours | 3 Hours |
| TDA | 20.47 | 11.16 | 9.28 |
| N-tert-butyl TDA | 13.64 | 10.20 | 8.95 |
| ar-tert-butyl TDA | 48.62 | 56.09 | 57.52 |
| N,ar-di-tert-butyl TDA | 7.84 | 9.66 | 10.4 |
| ar,ar-di-tert-butyl TDA | 8.33 | 11.96 | 12.68 |

These results show the excellent catalytic effect of aluminum chloride at only 170° C. The mono-ar-tert-butyl TDA had substantially peaked after only 2 hours.

The autoclave was then cooled to 150° C. and vented. Dealkylation at 150° C. proceeded as follows:

|  | Dealkylation Time (Hrs) | | |
| --- | --- | --- | --- |
|  | 0.5 | 1.0 | 2.0 |
| TDA | 13.08 | 15.59 | 20.24 |
| N-tert-butyl TDA | 8.80 | 7.56 | 6.06 |
| ar-tert-butyl TDA | 59.16 | 60.93 | 64.06 |
| N,ar-di-tert-butyl TDA | 6.93 | 4.70 | 2.10 |
| ar,ar-di-tert-butyl TDA | 10.50 | 9.41 | 6.12 |

The results show a sharp increase in the desired ar-tert-butyl TDA after only 2 hours. The dealkylation was continued at 160° C. and the ar-tert-butyl TDA content dropped to 44.35 percent after 2 additional hours while TDA content jumped to 48.78 percent. This shows the importance of monitoring the reaction product during dealkylation to detect the optimum dealkylation time under each different dealkylation condition. Once established, further analysis should not be required.

Example 7

This reaction was similar to Example 6 using aluminum chloride as the aluminum halide. The TDA change was doubled to give the following ratio: 20 moles TDA/1 equiv. Al/3 equiv. Cl. Alkylation was conducted at 170° C./1000 psig with the following results:

|  | Alkylation Time (Hrs) | | | | |
| --- | --- | --- | --- | --- | --- |
|  | 1 | 2 | 3 | 4 | 5 |
| TDA | 34.91 | 25.46 | 21.30 | 16.76 | 11.07 |
| N-tert-butyl TDA | 19.71 | 19.25 | 17.97 | 15.68 | 13.61 |
| ar-tert-butyl TDA | 36.95 | 43.06 | 45.93 | 50.53 | 53.96 |
| N,ar-di-tert-butyl TDA | 5.56 | 7.28 | 8.44 | 9.32 | 11.30 |
| ar,ar-di-tert-butyl TDA | 2.86 | 4.44 | 5.98 | 7.29 | 9.51 |

At this stage, the ar-tert-butyl TDA was still increasing. The autoclave was cooled to 112° C. and vented. It was then held at 157°-166° C. for 4 hours with the following results:

|  | Dealkylation Time (Hrs) | | | |
| --- | --- | --- | --- | --- |
|  | 1 | 2 | 3 | 4 |
| TDA | 16.11 | 17.31 | 23.12 | 27.05 |
| N-tert-butyl TDA | 13.91 | 10.38 | 8.22 | 6.46 |
| ar-tert-butyl TDA | 53.62 | 60.58 | 61.22 | 61.56 |
| N,ar-di-tert-butyl TDA | 7.84 | 4.22 | 1.94 | 1.00 |
| ar,ar-di-tert-butyl TDA | 7.69 | 7.01 | 4.96 | 3.32 |

The results show that the ar-tert-butyl TDA was about maximized after 2 hours. However, in this run, continuing dealkylation for 4 hours was beneficial because ar-tert-butyl TDA did not decrease whereas all three of the undesired N-tert-butyl TDA, N,ar-di-tert-butyl TDA and ar,ar-di-tert-butyl TDA continued to decrease while TDA suitable for recycle increased to 27.05 percent.

The following four examples show the detrimental effect of increasing the alkylation temperature to 225.C or higher on the yield of ar-tert-butyl TDA.

Examples 8-11

In these examples the catalyst was formed by adding AlCl₃ to TDA to give a ratio of 15 moles TDA per mole AlCl₃. The reaction pressure was 1000 psig isobutylene. The following table shows the alkylation temperature and the reaction composition for each temperature at the end of three hours.

| Ex. | Alkylation Temp, °C. | Reaction Composition at 3 Hours | | | | |
| --- | --- | --- | --- | --- | --- | --- |
|  |  | TDA | N-t-butyl TDA | ar-t-butyl TDA | N-ar-di-t-butyl TDA | ar,ar-di-t-butyl TDA |
| 8 | 175° | 12.45% | 11.78% | 57.84% | 9.91% | 7.20% |
| 9 | 205° | 25.64% | 11.05% | 52.97% | 5.73% | 3.23% |
| 10 | 225°[1] | 46.63% | 8.44% | 40.15% | 1.98% | 1.11% |
| 11 | 240° | 59.66% | 6.29% | 29.06% | 1.56% | 1.11% |
| 12 | 275°[1] | 78.24% | 2.15% | 17.23% | — | — |

[1]Two hour alkylation.

The following example is of interest as showing the effect of alkylation at 200° followed by further reaction under isobutylene pressure at 225° C. The results show that the reaction mixture seeks an equilibrium composition that depends on the temperature.

Example 13

This example was conducted by the standard procedure using ethylaluminum sesquichloride (EASC) as the catalyst source at a ratio of 5.5 moles TDA per one gram atom of Al (one gram atom of EASC is 0.5 gram mole). During the first five hours the isobutylene pressure was 1000 psig and the temperature was 200°-201° C. During the next three hours the temperature was held at 225° C. at 950-1000 psig isobutylene. The reaction composition during this period is shown in the following table.

|  | Alkylation Time (Hrs) | | | | | | | |
| --- | --- | --- | --- | --- | --- | --- | --- | --- |
|  | 1 | 2 | 3 | 4 | 5 | 6 | 7 | 8 |
| TDA | 46.36 | 39.80 | 35.90 | 33.82 | 30.83 | 50.68 | 50.65 | 49.76 |
| N-tert-butyl TDA | 10.10 | 10.38 | 9.92 | 9.83 | 9.61 | 6.89 | 7.03 | 7.20 |
| ar-tert-butyl TDA | 38.66 | 43.80 | 47.24 | 48.77 | 51.25 | 38.13 | 37.58 | 37.09 |
| N,ar-tert-butyl TDA | 2.61 | 3.34 | 3.88 | 4.26 | 4.70 | 1.72 | 1.72 | 1.8 |
| ar,ar-tert-butyl TDA | 1.41 | 1.86 | 2.24 | 2.48 | 2.80 | 0.96 | 0.95 | 0.96 |

At five hours at 200° C., the reaction composition is close to the composition of Example 9 at 205° C. When the temperature is increased to 225° C. while still under 950-1000 psig isobutylene, the composition equilibriates to about the same composition as in Example 10 which was carried out at 225° C. This demonstrates that the reaction composition is dependent on final reaction temperature and that ar-tert-butyl TDA is maximized at temperatures below 225° 1 C.

I claim:

1. A process for making mono-tert-butyl-toluenediamine, said process comprising:
   (A) forming a mixture of toluenediamine and an aluminum halide having the formula

   $$R_nAlX_{3-n} \qquad (I)$$

or

   $$R_3Al_2X_3 \qquad (II)$$

or mixtures thereof,
   wherein R is an alkyl group containing 1–10 carbon atoms, X is chlorine or bromine and n is 1 or 2 wherein the ratio of moles of toluenediamine:equivalents of Al:equivalents of X is in the range of 5–20:1.0:1–3, (B) reacting said mixture with isobutylene at a temperature of about 150°–220° C. and a pressure of about 500–3000 psig until the mono-tert-butyl toluenediamine content of the reaction mixture is substantially maximized, and (C) recovering said mono-tert-butyl toluenediamine.

2. A process of claim 1 wherein said aluminum halide is a $C_{1-10}$ alkylaluminum halide.

3. A process of claim 2 wherein said alkylaluminum halide is methylaluminum sesquichloride.

4. A process of claim 2 wherein said alkylaluminum halide is ethylaluminum sesquichloride.

5. A process of claim 2 wherein said alkylaluminum halide is dimethylaluminum chloride.

6. A process of claim 2 wherein said alkylaluminum chloride is methylaluminum dichloride.

7. A process of claim 2 wherein said alkylaluminum chloride is diethylaluminum chloride.

8. A process of claim 2 wherein said alkylaluminum halide is ethylaluminum dichloride.

9. A process of claim 1 further characterized by venting the reaction vessel after completion of the butylation and maintaining the reaction mixture at a temperature of about 130°–200° C. for a period of about 30 minutes to 4 hours whereby di-tert-butyl toluenediamine and N-tert-butyl-ar-tert butyl toluenediamine formed in the butylation reaction are converted to mono-ar-tert-butyl toluenediamine.

10. A process of claim 9 wherein said aluminum halide is a $C_{1-10}$ alkylaluminum halide.

11. A process of claim 10 wherein said alkylaluminum halide is methylaluminum sesquichloride.

12. A process of claim 10 wherein said alkylaluminum halide is ethylaluminum sesquichloride.

13. A process of claim 10 wherein said alkylaluminum halide is dimethylaluminum chloride.

14. A process of claim 10 wherein said alkylaluminum chloride is methylaluminum dichloride.

15. A process of claim 10 wherein said alkylaluminum chloride is diethylaluminum chloride.

16. A process of claim 10 wherein said alkylaluminum halide is ethylaluminum dichloride.

* * * * *